United States Patent
Hasegawa

(10) Patent No.: US 10,870,828 B2
(45) Date of Patent: Dec. 22, 2020

(54) CELL SURVIVAL RATE DETERMINING DEVICE

(71) Applicant: AZBIL CORPORATION, Chiyoda-ku (JP)

(72) Inventor: Norio Hasegawa, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 272 days.

(21) Appl. No.: 15/961,990

(22) Filed: Apr. 25, 2018

(65) Prior Publication Data

US 2018/0312797 A1    Nov. 1, 2018

(30) Foreign Application Priority Data

Apr. 26, 2017    (JP) .................................. 2017-086813

(51) Int. Cl.
*C12M 1/34*    (2006.01)
*G01N 21/64*    (2006.01)

(52) U.S. Cl.
CPC ......... *C12M 41/46* (2013.01); *G01N 21/6408* (2013.01); *G01N 21/6486* (2013.01)

(58) Field of Classification Search
None
See application file for complete search history.

(56) References Cited

U.S. PATENT DOCUMENTS

| 2010/0210927 A1* | 8/2010 | Gillies | A61B 5/0084 600/317 |
| 2012/0228519 A1* | 9/2012 | Gilmore | G01N 21/645 250/459.1 |
| 2017/0284940 A1* | 10/2017 | Butte | G01J 3/4406 |

FOREIGN PATENT DOCUMENTS

| JP | 2592114 | 3/1997 |
| JP | 4868879 | 2/2012 |
| JP | 2015-108549 A | 6/2015 |

OTHER PUBLICATIONS

Saskia M. Faassen, et al., "Fluorescence Spectroscopy and Chemometric Modeling for Bioprocess Monitoring", Sensors, 2015, 15, pp. 10271-10291.

M. J. Miller, et al., "Evaluation of the BioVigilant IMD-A™, A novel optical spectroscopy technology for the continuous and real-time environmental monitoring of viable and nonviable particles", PDA Journal of Pharmaceutical Science and Technology, 2009, vol. 63 (3), pp. 245-258.

Office Action dated Oct. 17, 2019 in corresponding Korean Patent Application No. 10-2018-0047953 (with English Translation), 9 pages.

* cited by examiner

*Primary Examiner* — Holly Kipouros
(74) *Attorney, Agent, or Firm* — Oblon, McClelland, Maier & Neustadt, L.L.P.

(57) ABSTRACT

A cell survival rate determining device includes a survival rate calculation unit calculating the survival rate of cells in a cell population based on a peak wavelength giving a peak intensity of autofluorescence emitted by the cell population and a peak wavelength of excitation light giving the peak intensity of autofluorescence; and a determination unit determining whether the calculated survival rate of cells is reliable or not based on an amount of a shift and a direction of the shift per unit time in the peak wavelength of autofluorescence and an amount of a shift and a direction of the shift per unit time in the peak wavelength of excitation light.

10 Claims, 12 Drawing Sheets

FIG. 7

| NUMBER OF DAYS OF CULTURE | SURVIVAL RATE (%) |
|---|---|
| 0 | 95 |
| 1 | 96 |
| 2 | 98 |
| 3 | 97 |
| 4 | 96 |
| 5 | 96 |
| 6 | 93 |
| 7 | 89 |
| 8 | 56 |
| 9 | 12 |

AVERAGE OF N=3

CELL SURVIVAL RATE DETERMINING DEVICE

CROSS-REFERENCE TO RELATED APPLICATIONS

The present application is based on and claims priority to Japanese Application No. 2017-086813, filed Apr. 26, 2017, the entire contents of which are incorporated herein by reference.

BACKGROUND DISCLOSURE

1. Field

The present disclosure relates to a cell culture technique and relates to a cell survival rate determining device.

2. Description of the Related Art

In the fields of bioprocess and cell culture, for example, in order to control the conditions of cell culture and judge the time of stopping cell culture, the life or death of cultured cells is determined to measure the survival rate. As a method for determining the life or death of cells, proposed is a method of coupling a fluorescent dye to a nucleic acid in a cell and determining the life or death of the cell by the intensity of excited fluorescence (for example, see Japanese Patent No. 2592114). There is known a method for determining the life or death of cells by staining with trypan blue that permeates through the cell membrane of dead cells and stains the cytoplasm of the dead cells blue.

However, staining reagents are expensive, and the process of staining cells is complicated. In addition, the staining reagents are often harmful to human bodies. Accordingly, the storage of staining reagents is required to be managed. In addition, it is difficult to subsequently culture the cells stained with a staining reagent, and the waste fluid is also required to be carefully treated. Herein, the cells emit autofluorescence (for example, see Saskia M. Faassen, et al., "Fluorescence Spectroscopy and Chemometric Modeling for Bioprocess Monitoring", Sensors, 2015, 15, 10271-10291; and M. J. Miller, et al., "Evaluation of the BioVigilant IMD-A, A novel optical spectroscopy technology for the continuous and real-time environmental monitoring of viable and nonviable particles. Part I. Review of the Technology and comparative studies with conventional methods", PDA Journal of Pharmaceutical Science and Technology, 2009, vol. 63 (3), 245-258). Accordingly, a method for determining the life or death of cells based on the autofluorescence emitted by the cells, without using a staining reagent, has been proposed (for example, see Japanese Patent No. 4868879).

SUMMARY

In the method disclosed in Japanese Patent No. 4868879, the viability of cells is determined by a change in the intensity of autofluorescence of the cells. However, according to the findings of the present inventor, the intensity of autofluorescence of cells can also be changed by a factor other than the viability of the cells. Accordingly, when the intensity of autofluorescence of cells is changed by a factor other than the viability of the cells, there is a risk of falsely determining that the viability of the cells has changed despite of no change in the viability of the cells. Accordingly, it is an object of the present disclosure to provide a cell survival rate determining device and a cell survival rate determining method that can calculate a survival rate of cells and determine whether the calculated survival rate of cells is reliable or not.

According to a first aspect of the present disclosure, provided is a cell survival rate determining device including a survival rate calculation unit calculating a survival rate of cells in a cell population based on a peak wavelength giving a peak intensity of autofluorescence emitted by the cell population and a peak wavelength of excitation light giving the peak intensity of autofluorescence; and a determination unit determining whether the calculated survival rate of cells is reliable or not based on an amount of a shift and a direction of the shift per unit time in the peak wavelength of autofluorescence and an amount of a shift and a direction of the shift per unit time in the peak wavelength of excitation light.

In the cell survival rate determining device according to the first aspect, the determination unit may calculate a vector of the sum of a vector representing an amount of a shift and a direction of the shift per unit time in the peak wavelength of autofluorescence and a vector representing an amount of a shift and a direction of the shift per unit time in the peak wavelength of excitation light in a coordinate system using the wavelength of autofluorescence and the wavelength of excitation light as coordinate components.

In the cell survival rate determining device according to the first aspect, when the size of the vector of the sum is not lower than a predetermined threshold and the direction of the vector of the sum is within a predetermined range, the determination unit may determine that the calculated survival rate of cells is reliable.

In the cell survival rate determining device according to the first aspect, when the size of the vector of the sum is not lower than a predetermined threshold and the direction of the vector of the sum is out of a predetermined range, the determination unit may determine that the calculated survival rate of cells is unreliable.

In the cell survival rate determining device according to the first aspect, the cell population may be suspension-cultured.

In the cell survival rate determining device according to the first aspect, individual cells of the cell population may be Chinese hamster ovary (CHO) cells.

According to a second aspect of the present disclosure, provided is a cell survival rate determining device including a survival rate calculation unit calculating a survival rate of cells in a cell population based on at least first and second light intensities selected from the intensity of autofluorescence in a first wavelength bandwidth and the intensity of autofluorescence in a second wavelength bandwidth emitted by individual cells of the cell population and the intensity of scattered light generated in individual cells of the cell population; and a determination unit determining whether the calculated survival rate of cells is reliable or not based on an amount of a change and a direction of the change per unit time in the first light intensity and an amount of a change and a direction of the change per unit time in the second light intensity.

In the cell survival rate determining device according to the second aspect, three light intensities: the intensity of autofluorescence in a first wavelength bandwidth, the intensity of autofluorescence in a second wavelength bandwidth, and the intensity of scattered light, may be selected.

In the cell survival rate determining device according to the second aspect, the determination unit may calculate a vector of the sum of a vector representing an amount of a change and a direction of the change per unit time in the first light intensity and a vector representing an amount of a change and a direction of the change per unit time in the second light intensity in a coordinate system using the first light intensity and the second light intensity as coordinate components.

In the cell survival rate determining device according to the second aspect, when the size of the vector of the sum is not lower than a predetermined threshold and the direction of the vector of the sum is within a predetermined range, the determination unit may determine that the calculated survival rate of cells is reliable.

In the cell survival rate determining device according to the second aspect, when the size of the vector of the sum is not lower than a predetermined threshold and the direction of the vector of the sum is out of a predetermined range, the determination unit may determine that the calculated survival rate of cells is unreliable.

In the cell survival rate determining device according to the second aspect, the cell population may be suspension-cultured.

In the cell survival rate determining device according to the second aspect, individual cells of the cell population may be Chinese hamster ovary (CHO) cells.

The present disclosure can provide a cell survival rate determining device and a cell survival rate determining method that can calculate a survival rate of cells and determine whether the calculated survival rate of cells is reliable or not.

BRIEF DESCRIPTION OF THE DRAWINGS

FIG. 7 is a table showing a relationship between the number of days of culture and the survival rate of cells according to Example 1;

DETAILED DESCRIPTION

Embodiments of the present disclosure will now be described. In the following description of the drawings, the same or similar portions are denoted by the same or similar reference signs. However, the drawings are schematic. Accordingly, the specific dimensions and the like should be determined by considering the following description. It should be also noted that the drawings may include portions which differ from one drawing to another in dimensional relationship and ratios.

It should not be understood that the description and drawings constituting a part of this disclosure limit the present disclosure. From this disclosure, various alternative embodiments, examples, and operational techniques will be apparent to those skilled in the art. Accordingly, it should be understood that the present disclosure also encompasses various embodiments and the like not described herein.

First Embodiment

Figure 1:
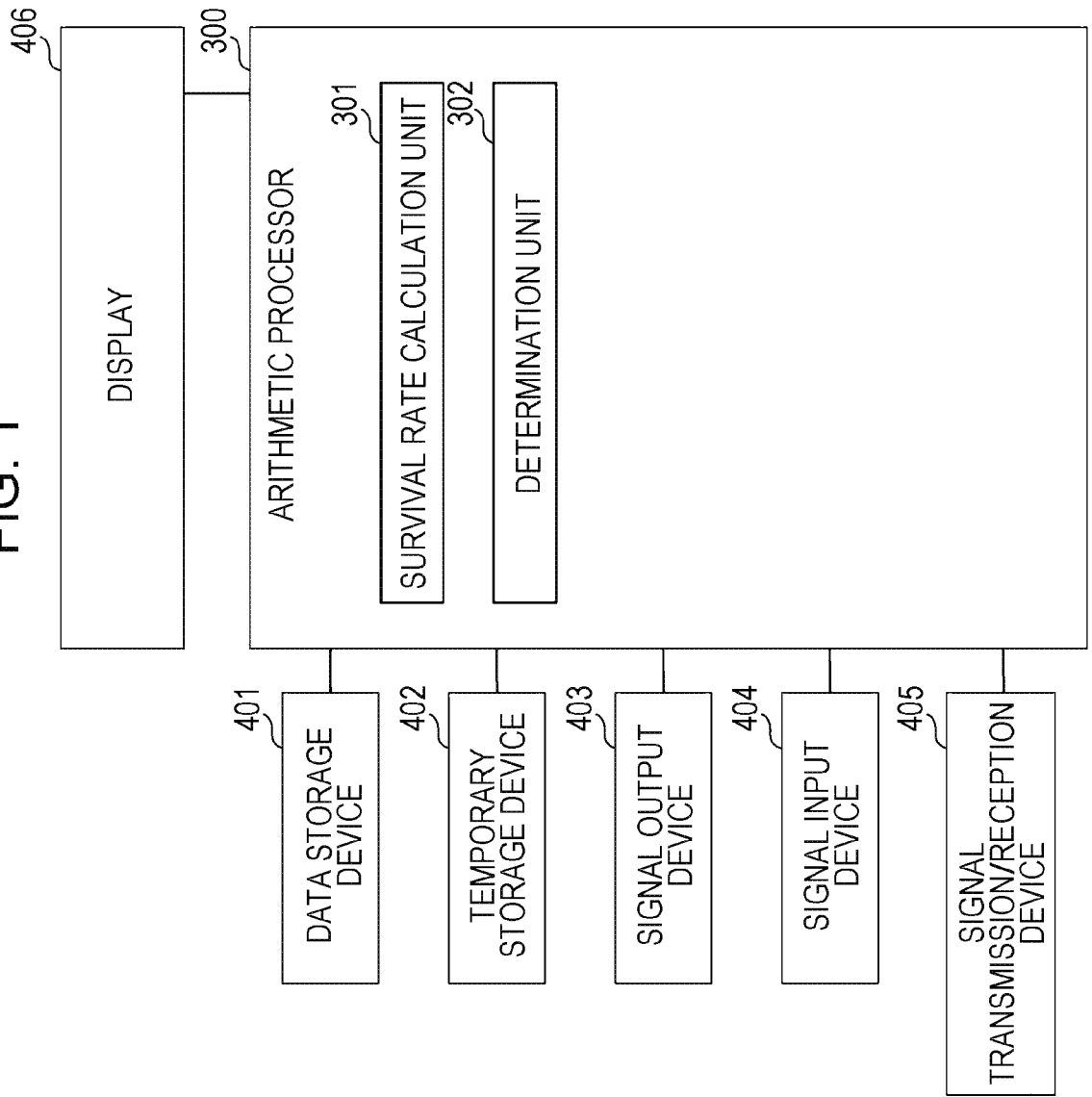
FIG. 1 is a schematic diagram of a cell survival rate determining device according to a first embodiment.
Figure 2:
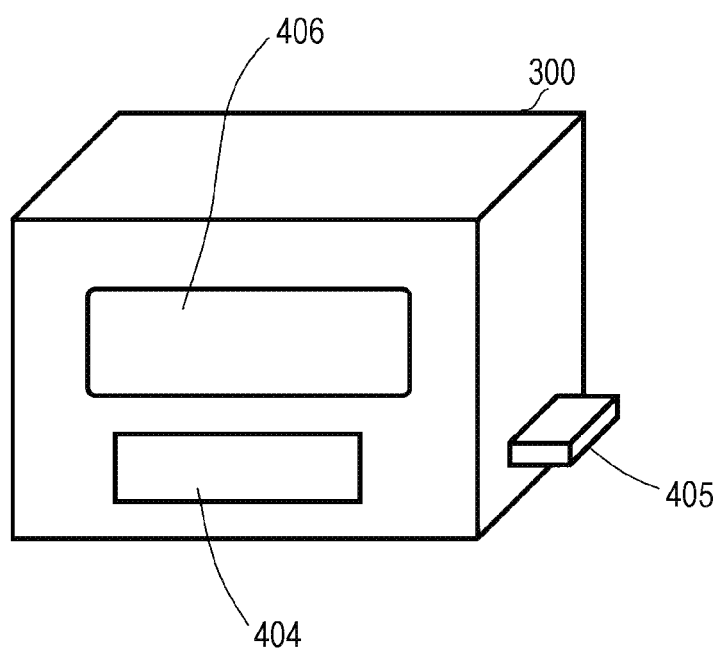
FIG. 2 is a schematic diagram of a cell survival rate determining device according to the first embodiment.

The cell survival rate determining device according to a first embodiment, as shown in FIGS. 1 and 2, includes a survival rate calculation unit 301 calculating the survival rate of cells in a cell population based on a peak wavelength giving a peak intensity of autofluorescence emitted by the cell population and a peak wavelength of excitation light giving the peak intensity of autofluorescence; and a determination unit 302 determining whether the calculated survival rate of cells is reliable or not based on an amount of a shift and a direction of the shift per unit time in the peak wavelength of autofluorescence and an amount of a shift and a direction of the shift per unit time in the peak wavelength of excitation light. The survival rate calculation unit 301 and the determination unit 302 are included in, for example, an arithmetic processor 300. Herein, the unit time is, for example, 24 hours, but it may be any fixed period of time and may be shorter than 24 hours or longer than 24 hours.

The cells are, for example, suspension-cultured cells. In suspension culture, spherical cells grow in a state of floating in a culture medium without adhering to the bottom of the incubator. The cells may be adherent cultured cells. Examples of the cells include all kinds of cells. For example, the cells are antibody-producing cells. Examples of the antibody-producing cells include Chinese hamster ovary (CHO) cells. The term "CHO cell" includes established CHO cell lines. In addition, the term "CHO cell" includes subspecies, such as CHO-K1 cells and dihydrofolate reductase (DHFR) deficient CHO-DG44 cells.

According to the findings by the present inventor, it is possible to previously acquire a relationship among the peak wavelength of autofluorescence, the peak wavelength of excitation light, and the survival rate of cells in a cell population. For example, the peak wavelength of autofluorescence and the peak wavelength of excitation light in a solution containing cells are measured every day from the start of cell culture; and the proportion of dead cells or living cells in the solution containing cells is measured by a known method, such as trypan blue staining. Thus, a relationship among the peak wavelength of autofluorescence, the peak wavelength of excitation light, and the survival rate of cells in a cell population is acquired. The relationship is given as, for example, a function with the peak wavelength of autofluorescence and the peak wavelength of excitation light as independent variables and the survival rate of cells in the cell population as a dependent variable.

The survival rate calculation unit 301 acquires a measured value of the peak wavelength of autofluorescence emitted by a cell population and a measured value of the peak wavelength of excitation light corresponding to the peak wavelength of autofluorescence. The measured value of the peak wavelength of autofluorescence emitted by a cell population and the measured value of the peak wavelength of excitation light are obtained by measuring the spectrum of autofluorescence while scanning the wavelength of excitation light. The spectrum of autofluorescence obtained while scanning the wavelength of excitation light is also called excitation-emission matrix (EEM). The survival rate calculation unit 301 may acquire a measured value of the peak wavelength of autofluorescence emitted by a cell population and a measured value of the peak wavelength of excitation light corresponding to the peak wavelength of autofluorescence as those measured by another measuring device. Furthermore, the survival rate calculation unit 301 calculates the survival rate of cells in the cell population using a previously acquired relationship among the peak wavelength of autofluorescence, the peak wavelength of excitation light, and the survival rate of cells in a cell population and the measured values of the peak wavelength of autofluorescence and the peak wavelength of excitation light.

The determination unit 302 acquires time series data of a measured value of the peak wavelength of autofluorescence emitted by a cell population. The determination unit 302 acquires time series data of a measured value of the peak wavelength of excitation light corresponding to the peak wavelength of autofluorescence. The time series data of a measured value of the peak wavelength of autofluorescence emitted by a cell population and the time series data of a measured value of the peak wavelength of excitation light corresponding to the peak wavelength of autofluorescence are obtained by measuring the spectrum of autofluorescence while scanning the wavelength of excitation light repeatedly over time.

The determination unit 302 calculates a vector of the sum of a vector representing an amount of a shift and a direction of the shift per unit time in the peak wavelength of autofluorescence and a vector representing an amount of a shift and a direction of the shift per unit time in the peak wavelength of excitation light in a coordinate system using the wavelength of autofluorescence and the wavelength of excitation light as coordinate components.

Figure 3:
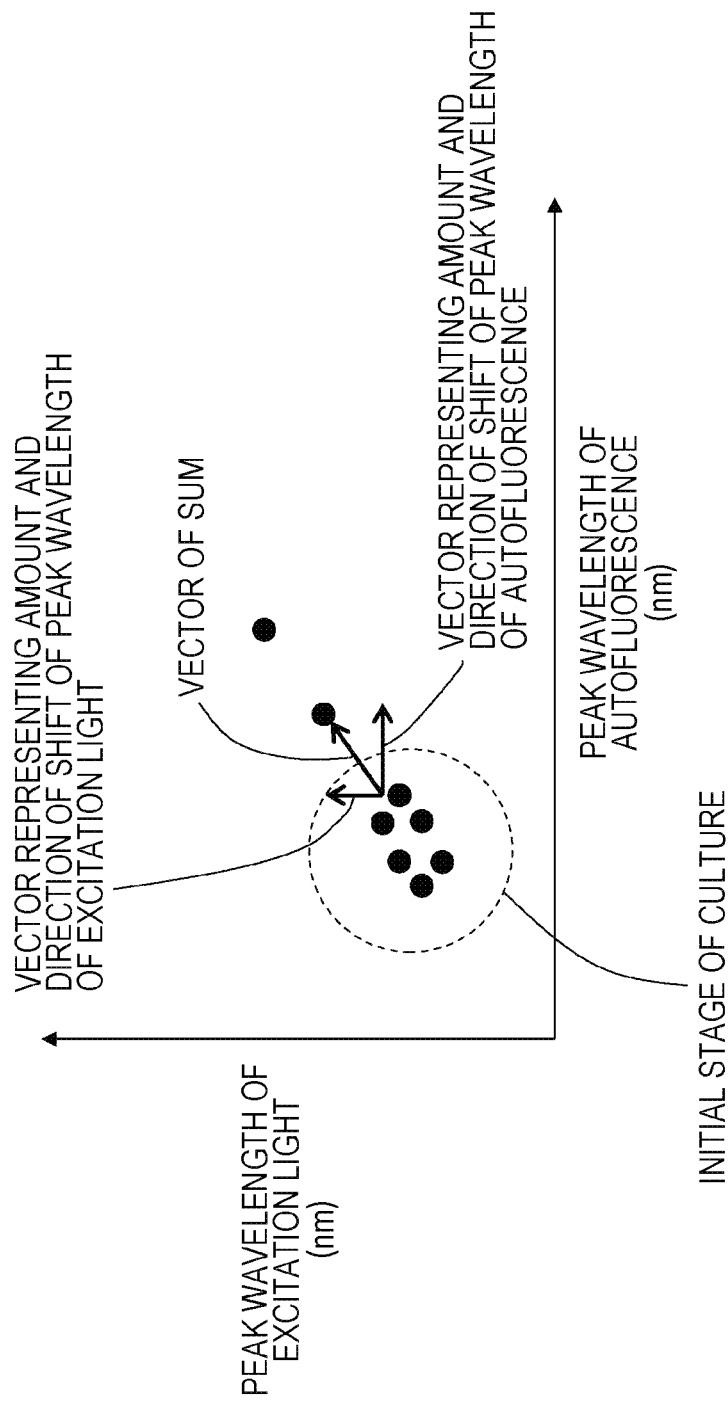
FIG. 3 is a schematic graph showing a relationship between the peak wavelength of autofluorescence of cells and the peak wavelength of excitation light according to the first embodiment.

Herein, according to the findings by the present inventor, as shown in FIG. 3, in the initial stage of culture of a cell population, when the number of living cells dominates the number of dead cells and the survival rate of cells is high, in a predetermined unit time, the amount of a shift in the peak wavelength of autofluorescence and the amount of a shift in the peak wavelength of excitation light both tend to be small. In addition, in a predetermined unit time, the direction of a shift in the peak wavelength of autofluorescence and the direction of a shift in the peak wavelength of excitation light both tend to be random.

However, if the proportion of dead cells in a cell population increases with the number of days of cell culture, in a predetermined unit time, the amount of a shift in the peak wavelength of autofluorescence and the amount of a shift in the peak wavelength of excitation light both tend to increase.

In addition, in a predetermined unit time, the direction of a shift in the peak wavelength of autofluorescence and the direction of a shift in the peak wavelength of excitation light both tend to be constant. Specifically, the peak wavelength of autofluorescence and the peak wavelength of excitation light tend to shift toward the long wavelength side.

Accordingly, if the proportion of dead cells in a cell population increases, the size of a vector of the sum of a vector representing an amount of a shift and a direction of the shift per unit time in the peak wavelength of autofluorescence and a vector representing an amount of a shift and a direction of the shift per unit time in the peak wavelength of excitation light is larger a predetermined threshold, and the direction of the vector of the sum tends to be within a predetermined range.

The predetermined threshold of the size of a vector of the sum is set by, for example, previously measuring the size of a vector of the sum when the proportion of dead cells in a cell population increased. The predetermined range of the direction of a vector of the sum is set by previously measuring the direction of a vector of the sum when the proportion of dead cells in a cell population increased. These thresholds may be set by, for example, main component analysis, a partial least-square (PLS) method, and discrimination analysis.

When the direction of a vector of the sum is out of a predetermined range although the size of the vector of the sum per unit time is higher than a predetermined threshold, it is assumed that at least one of the peak wavelength of autofluorescence and the peak wavelength of excitation light shifted by a factor other than an increase in the proportion of dead cells in a cell population. Examples of the factor other than an increase in the proportion of dead cells include contamination of other fluorescent particles and a change in intensity of background light.

Accordingly, the determination unit 302 shown in FIG. 1 determines that the survival rate of cells calculated by the survival rate calculation unit 301 is reliable when the size of a vector of the sum per unit time is not lower than a predetermined threshold and the direction of the vector of the sum per unit time is within a predetermined range. In addition, the determination unit 302 determines that the survival rate of cells calculated by the survival rate calculation unit 301 is unreliable when the size of a vector of the sum per unit time is not lower than a predetermined threshold and the direction of the vector of the sum per unit time is out of a predetermined range.

The determination unit 302 may perform the determination using an abnormality detection algorithm. For example, the abnormality detection algorithm may be based on a one class support vector machine, abnormal value detection (LOF: Local Outlier Factor), Mahalanobis distance, and neural network.

The arithmetic processor 300 is connected to, for example, a data storage device 401. The data storage device 401 stores a relationship among the peak wavelength of autofluorescence, the peak wavelength of excitation light, and the survival rate of cells of a cell population previously acquired as described above. The data storage device 401 also stores a predetermined threshold of the size of a vector of the sum. The data storage device 401 further stores a predetermined range of the direction of a vector of the sum.

The arithmetic processor 300 may be connected to, for example, a temporary storage device 402, a signal output device 403, a signal input device 404, a signal transmission/reception device 405, and a display 406. The temporary storage device 402 temporarily stores information in the calculation process by the arithmetic processor 300. The signal output device 403 outputs signals processed by the arithmetic processor 300. The signal input device 404 inputs signals to be processed by the arithmetic processor 300. The signal transmission/reception device 405 transmits and receives signals to and from an external device. The display 406 displays information in the processing by the arithmetic processor 300 and information on the results of the processing.

The cell survival rate determining device according to the first embodiment described above can measure the survival rate of cells in a cell population by measuring the peak wavelength of autofluorescence in the cell population and the peak wavelength of excitation light without determining the life or death of individual cells. Furthermore, the cell survival rate determining device according to the first embodiment can determine whether the calculated survival rate of cells is reliable or not.

For example, in a bioprocess, such as antibody drug production, it is important to determine the time of stopping the culture of antibody-producing cells based on the survival rate of the antibody-producing cells, for maximizing the antibody production efficiency of the cells. The cell survival rate determining device according to the first embodiment can determine the time of stopping the culture of antibody-producing cells based on the survival rate of cells that has been determined to be reliable.

Second Embodiment

In the cell survival rate determining device according to a second embodiment, the survival rate calculation unit 301 shown in FIG. 1 calculates the survival rate of cells in a cell population based on at least first and second light intensities selected from the intensity of autofluorescence in a first wavelength bandwidth and the intensity of autofluorescence in a second wavelength bandwidth different from the first wavelength bandwidth emitted by individual cells of the cell population and the intensity of scattered light generated in individual cells of the cell population. The determination unit 302 determines whether the calculated survival rate of cells is reliable or not based on an amount of a change and a direction of the change per unit time in the first light intensity and an amount of a change and a direction of the change per unit time in the second light intensity.

According to the findings by the present inventor, it is possible to previously acquire a relationship between at least first and second light intensities and the survival rate of cells in a cell population. For example, at least first and second light intensities in a solution containing cells are measured every day from the start of cell culture; and the proportion of dead cells or living cells in the solution containing cells is measured by a known method, such as trypan blue staining. Thus, a relationship between at least the first and second light intensities and the survival rate of cells in the cell population is acquired. The relationship is given as, for example, a function with at least the first and second light intensities as independent variables and the survival rate of cells in the cell population as a dependent variable.

An example in which the intensity of autofluorescence in a first wavelength bandwidth and the intensity of autofluorescence in a second wavelength bandwidth emitted by individual cells of a cell population and the intensity of scattered light generated in individual cells of the cell population are all selected will be described below.

The survival rate calculation unit 301 acquires a measured value of the intensity of autofluorescence in a first wavelength bandwidth and a measured value of the intensity of autofluorescence in a second wavelength bandwidth emitted by individual cells of a cell population and a measured value of the intensity of scattered light generated in individual cells of the cell population. The intensity of autofluorescence in a first wavelength bandwidth, the intensity of autofluorescence in a second wavelength bandwidth, and the intensity of scattered light are measured by irradiating individual cells of the cell population with excitation light. The wavelength of the excitation light is, for example, 340 nm or more and 410 nm or less, but is not limited thereto.

Furthermore, the survival rate calculation unit 301 calculates the survival rate of cells in a cell population using a previously acquired relationship among the intensity of autofluorescence in a first wavelength bandwidth, the intensity of autofluorescence in a second wavelength bandwidth, and the intensity of scattered light, a measured value of the intensity of autofluorescence in the first wavelength bandwidth, a measured value of the intensity of autofluorescence in the second wavelength bandwidth, and a measured value of the intensity of scattered light.

The determination unit 302 acquires time series data of a measured value of the intensity of autofluorescence in a first wavelength bandwidth and time series data of a measured value of the intensity of autofluorescence in a second wavelength bandwidth emitted by individual cells of a cell population and time series data of a measured value of the intensity of scattered light generated in individual cells of the cell population. These time series data are obtained by irradiating individual cells of a cell population with excitation light and measuring the intensity of autofluorescence in the first wavelength bandwidth, the intensity of autofluorescence in the second wavelength bandwidth, and the intensity of the scattered light repeatedly over time.

The determination unit 302 calculates a vector of the sum of a vector representing an amount of a change and a direction of the change per unit time in the intensity of autofluorescence in a first wavelength bandwidth, a vector representing an amount of a change and a direction of the change per unit time in the intensity of autofluorescence in a second wavelength bandwidth, and a vector representing an amount of a change and a direction of the change per unit time in the intensity of scattered light in a coordinate system using the intensity of autofluorescence in the first wavelength bandwidth, the intensity of autofluorescence in the second wavelength bandwidth, and the intensity of scattered light as coordinate components.

Figure 4:
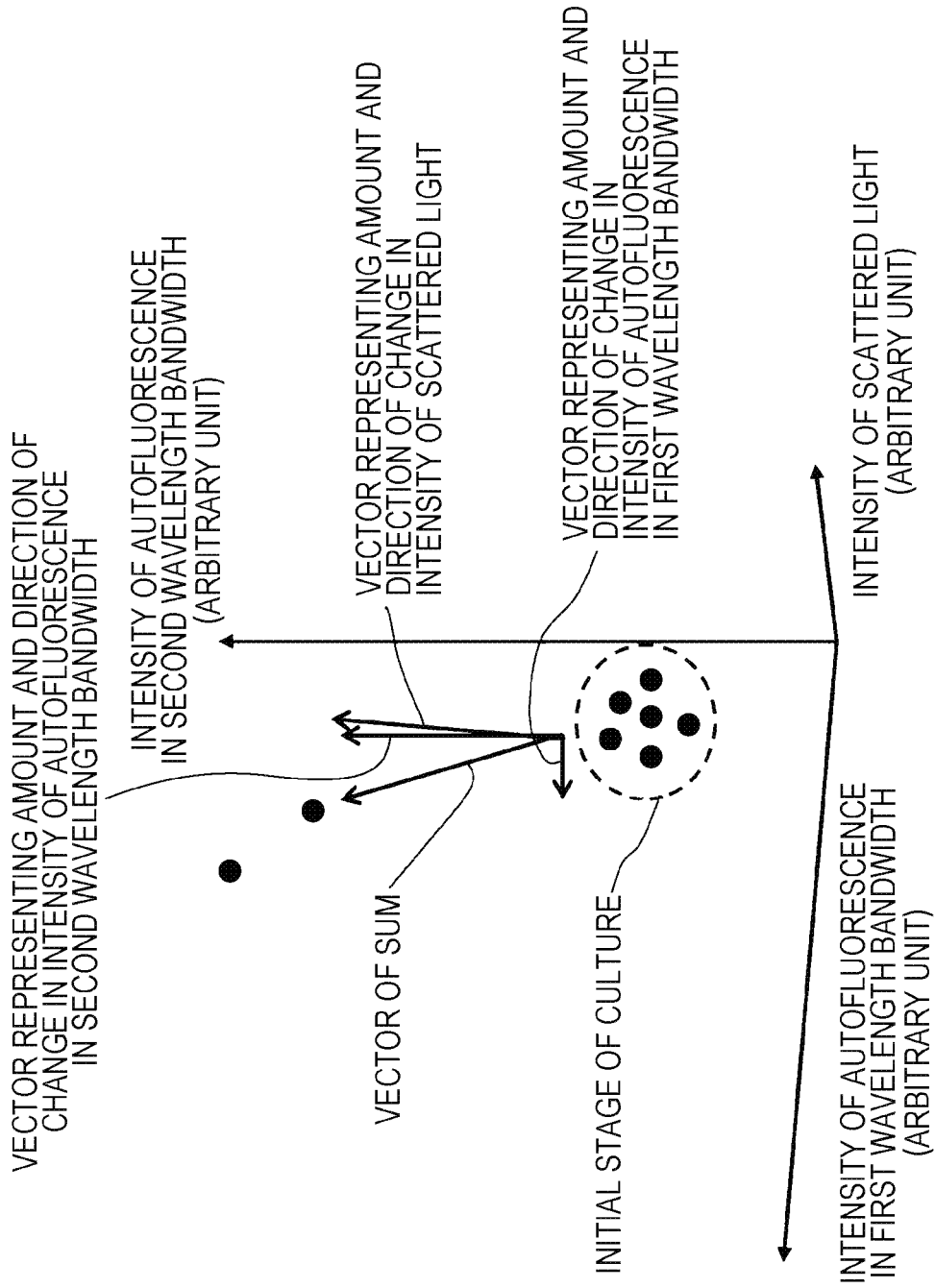
FIG. 4 is a schematic graph showing a relationship among the intensity of autofluorescence in a first wavelength bandwidth, the intensity of autofluorescence in a second wavelength bandwidth, and the intensity of scattered light according to a second embodiment.

Herein, according to the findings by the present inventor, as shown in FIG. 4, in the initial stage of culture of a cell population, when the number of living cells dominates the number of dead cells and the survival rate of cells is high, in a predetermined unit time, the amount of a change in the intensity of autofluorescence in a first wavelength bandwidth, the amount of a change in the intensity of autofluorescence in a second wavelength bandwidth, and the amount of a change in the intensity of scattered light all tend to be small. In addition, in a predetermined unit time, the direction of a change in the intensity of autofluorescence in the first wavelength bandwidth, the direction of a change in the intensity of autofluorescence in the second wavelength bandwidth, and the direction of a change in the intensity of scattered light all tend to be random.

However, if the proportion of dead cells in a cell population increases with the number of days of cell culture, in a predetermined unit time, the amount of a change in the intensity of autofluorescence in a first wavelength bandwidth, the amount of a change in the intensity of autofluorescence in a second wavelength bandwidth, and the amount of a change in the intensity of scattered light all tend to increase. In addition, in a predetermined unit time, the direction of a change in the intensity of autofluorescence in the first wavelength bandwidth, the direction of a change in the intensity of autofluorescence in the second wavelength bandwidth, and the direction of a change in the intensity of scattered light all tend to be constant.

Accordingly, if the proportion of dead cells in a cell population increases, the size of a vector of the sum of a vector representing an amount of a change and a direction of the change per unit time in the intensity of autofluorescence in a first wavelength bandwidth, a vector representing an amount of a change and a direction of the change per unit time in the intensity of autofluorescence in a second wavelength bandwidth, and a vector representing an amount of a change and a direction of the change per unit time in the intensity of scattered light is larger a predetermined threshold, and the direction of the vector of the sum tends to be within a predetermined range.

The predetermined threshold of the size of a vector of the sum is set by, for example, previously measuring the size of a vector of the sum when the proportion of dead cells in a cell population increased. The predetermined range of the direction of a vector of the sum is set by previously measuring the direction of a vector of the sum when the proportion of dead cells in a cell population increased.

When the direction of a vector of the sum is out of a predetermined range although the size of the vector of the sum per unit time is higher than a predetermined threshold, it is assumed that at least one of the intensity of autofluorescence in a first wavelength bandwidth, the intensity of autofluorescence in a second wavelength bandwidth, and the intensity of scattered light changed by a factor other than an increase in the proportion of dead cells in a cell population. Examples of the factor other than an increase in the proportion of dead cells include a change in the intensity of autofluorescence due to metabolism in cells, contamination of other fluorescent particles, and a change in intensity of background light.

Accordingly, the determination unit 302 shown in FIG. 1 determines that the survival rate of cells calculated by the survival rate calculation unit 301 is reliable when the size of a vector of the sum per unit time is not lower than a predetermined threshold and the direction of the vector of the sum per unit time is within a predetermined range. In addition, the determination unit 302 determines that the survival rate of cells calculated by the survival rate calculation unit 301 is unreliable when the size of a vector of the sum per unit time is not lower than a predetermined threshold and the direction of the vector of the sum per unit time is out of a predetermined range.

The arithmetic processor 300 is connected to, for example, a data storage device 401. The data storage device 401 stores a relationship between at least first and second light intensities and the survival rate of cells of a cell population previously acquired as described above. The data storage device 401 also stores a predetermined threshold of the size of a vector of the sum. The data storage device 401 further stores a predetermined range of the direction of a vector of the sum.

Other components of the cell survival rate determining device according to the second embodiment are the same as those in the first embodiment. The cell survival rate determining device according to the second embodiment also can determine whether the calculated survival rate of cells is reliable or not.

Third Embodiment

Figure 5:
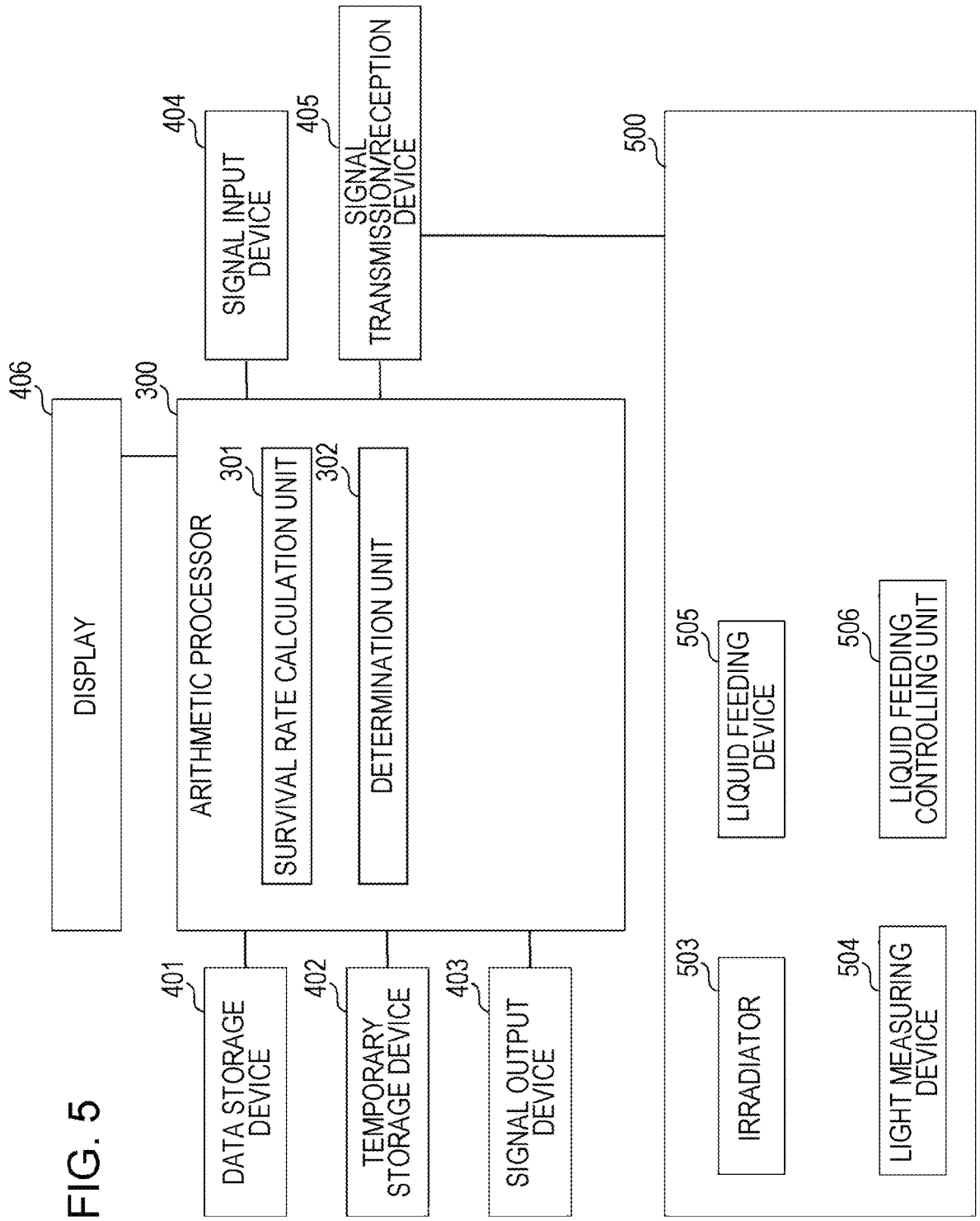
FIG. 5 is a schematic diagram of a cell survival rate determining device according to a third embodiment.
Figure 6:
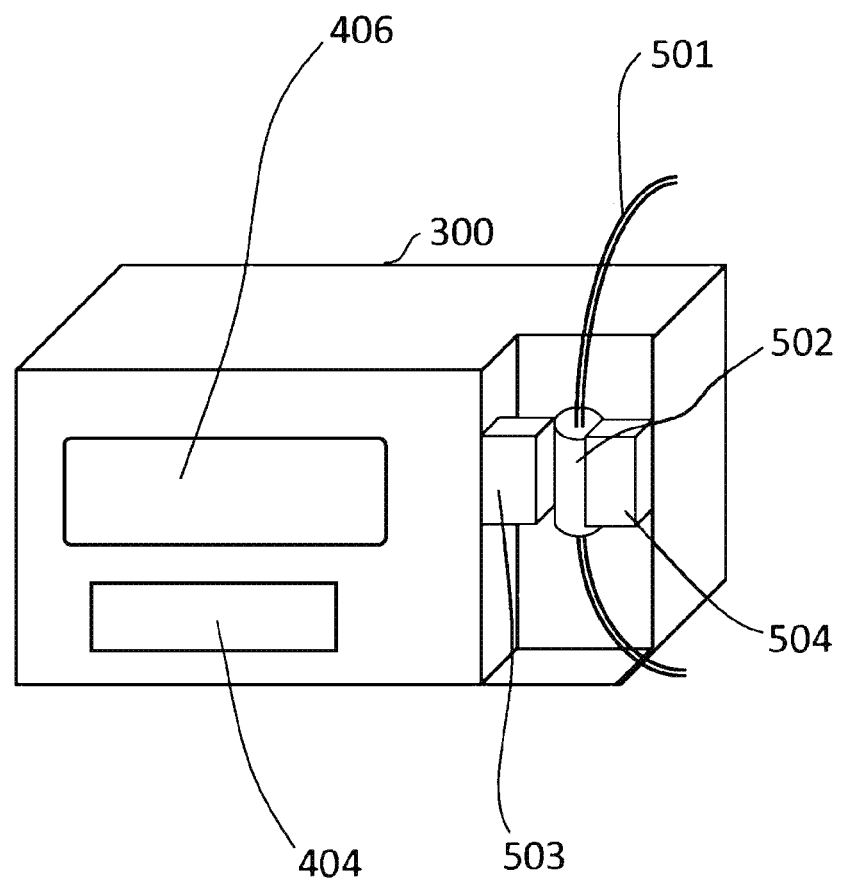
FIG. 6 is a schematic diagram of a cell survival rate determining device according to the third embodiment.

The cell survival rate determining device according to a third embodiment further includes an optical particle detector 500, as shown in FIGS. 5 and 6. The optical particle detector 500 includes, for example, a detachable flow channel 501 in which a solution containing cells flows, a detachable measuring cuvette 502 connected to the flow channel 501, an irradiator 503 irradiating the inside of the measuring cuvette 502 with measurement light, and a light measuring device 504 measuring the intensities of scattered light and fluorescence generated in the measuring cuvette 502 irradiated with the measurement light.

The solution containing cells flows in the flow channel 501 by means of a liquid feeding device 505. The liquid feeding device 505 is controlled by a liquid feeding controlling unit 506 to set, for example, the flow rate of the solution. The flow channel 501 can be detached from the optical particle detector 500. The detached flow channel 501 may be washed or may be replaced with a new clean flow channel 501. The measuring cuvette 502 is formed of a transparent material that is transmissive the measurement light and scattered light. Examples of the material of the measuring cuvette 502 include, but not limited to, quartz glass. The measuring cuvette 502 can be detached from the optical particle detector 500. The detached measuring cuvette 502 may be washed or may be replaced with a new clean measuring cuvette 502.

When the flow channel 501 and the measuring cuvette 502 are not clean, there is a risk that the cells measured last time remain in the flow channel 501 and the measuring cuvette 502 and affect the subsequent measurement. In contrast to this, since the flow channel 501 and the measuring cuvette 502 according to the third embodiment are detachable from the optical particle detector 500, it is easy to clean the flow channel 501 and the measuring cuvette 502.

The irradiator 503 includes, for example, a laser light source and a controller for the laser light source. The irradiator 503 irradiates the inside of the measuring cuvette 502 with measurement light, such as laser light. A lens may be arranged such that the measuring light focuses in the measuring cuvette 502. The irradiation of cells in the measuring cuvette 502 with measuring light generates Mie scattered light in the cells. In addition, the cells emit autofluorescence. The light measuring device 504 measures the intensities of the scattered light generated in the cells and the autofluorescence emitted by the cells. The intensities of scattered light and autofluorescence measured by the light measuring device 504 are transmitted to the survival rate calculation unit 301 via, for example, a signal transmission/reception device 405.

The other components of the cell survival rate determining device according to the third embodiment are the same as those in the second embodiment, and descriptions thereof are omitted.

Example 1

A medium (CD OptiCHO, registered trademark, protein-free, animal-derived ingredient-free, manufactured by Invitrogen) supplemented with L-glutamine (final concentration: 6 mmol/L) and Anti-Clumping Agent (final concentration: 1%) was prepared. CHO-K1 cells producing Trastuzumab were suspension-cultured in this medium at 37° C. in the presence of 5% $CO_2$. After the start of the suspension culture, the medium containing the cells was sampled on a regular basis.

The cells contained in the sampled medium were stained with trypan blue, and the total number of the cells and the number of the stained cells were counted with a cell counter. The stained cells were determined to be dead cells. The survival rate of the cells was calculated from the result of the determination. As a result, as shown in FIG. 7, the survival rate of the cells sharply decreased after Day 8 of the culture.

The sampled medium was centrifuged, and the precipitated cells were suspended in phosphate buffered saline (PBS). This suspension was analyzed with a spectrofluorometer (FP-8500, manufactured by JASCO Corporation) to obtain an excitation-emission matrix (EEM). The EEM is a three-dimensional matrix consisting of the wavelength of excitation light, the wavelength of autofluorescence, and the intensity of autofluorescence. In the analysis, in order to remove stray light due to scattering, a filter transmitting light having a wavelength longer than 385 nm was used in a fluorescent detector.

Figure 8:
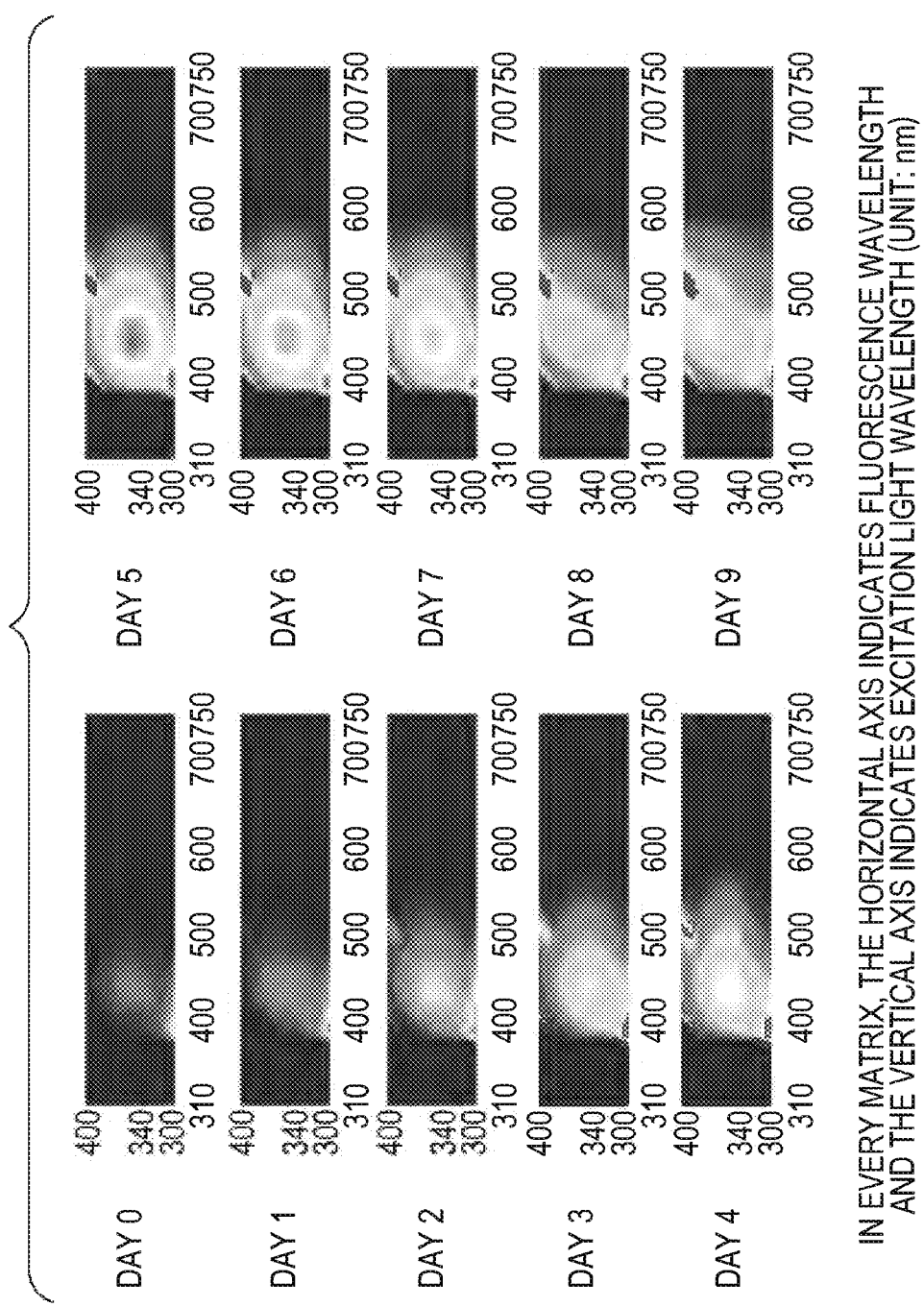
FIG. 8 shows excitation-emission matrix on each day of the culture according to Example 1.

FIG. 8 shows the resulting EEMs. Analysis of the EEMs showed that until Day 7 of the culture showing high survival rates of cells, the peak wavelength of autofluorescence was around 450 nm and the peak wavelength of excitation light corresponding to the peak wavelength of autofluorescence was around 340 nm. However, after Day 8 of the culture showing decreased survival rates of cells to about half, the peak wavelength of autofluorescence shifted to around 460 nm and the peak wavelength of excitation light corresponding to the peak wavelength of autofluorescence shifted to around 360 nm.

Figure 9:
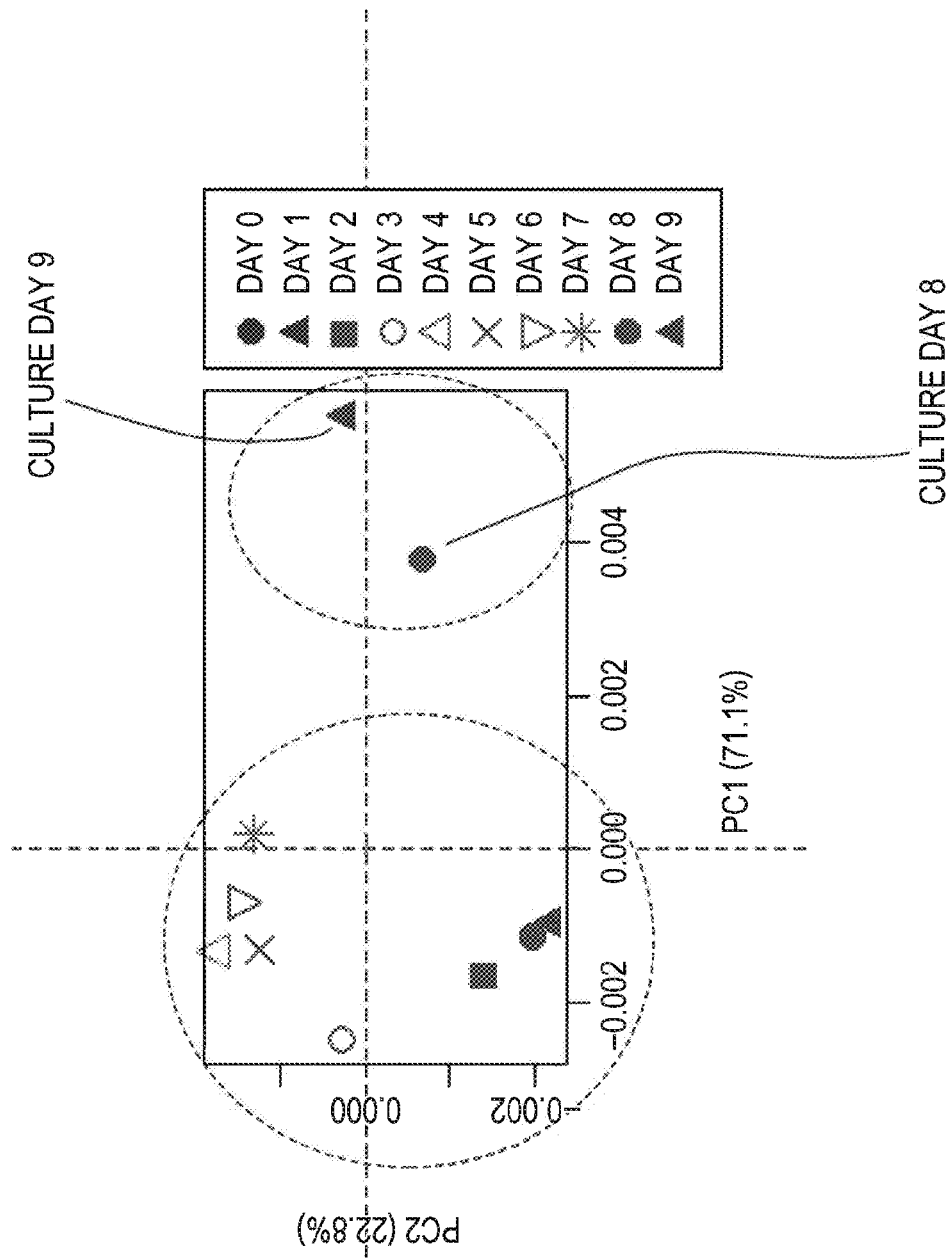
FIG. 9 is a graph showing the results of main component analysis according to Example 1.

Main component analysis of the EEMs shown in FIG. 8 showed that as shown in FIG. 9, the EEMs of Day 8 and Day 9 of the culture were apart from the EEMs of Day 0 to Day 7 of the culture.

In parallel with the measurement of EEMs, the sampled medium was diluted at a predetermined rate, and the cells contained in the medium were each irradiated with laser light using a particle detector (IMD-W, manufactured by Azbil Corporation) to measure the intensity of Mie scattered light generated in each of the cells and the intensities of autofluorescence emitted by the cells in blue bandwidth and green bandwidth.

Figure 10:
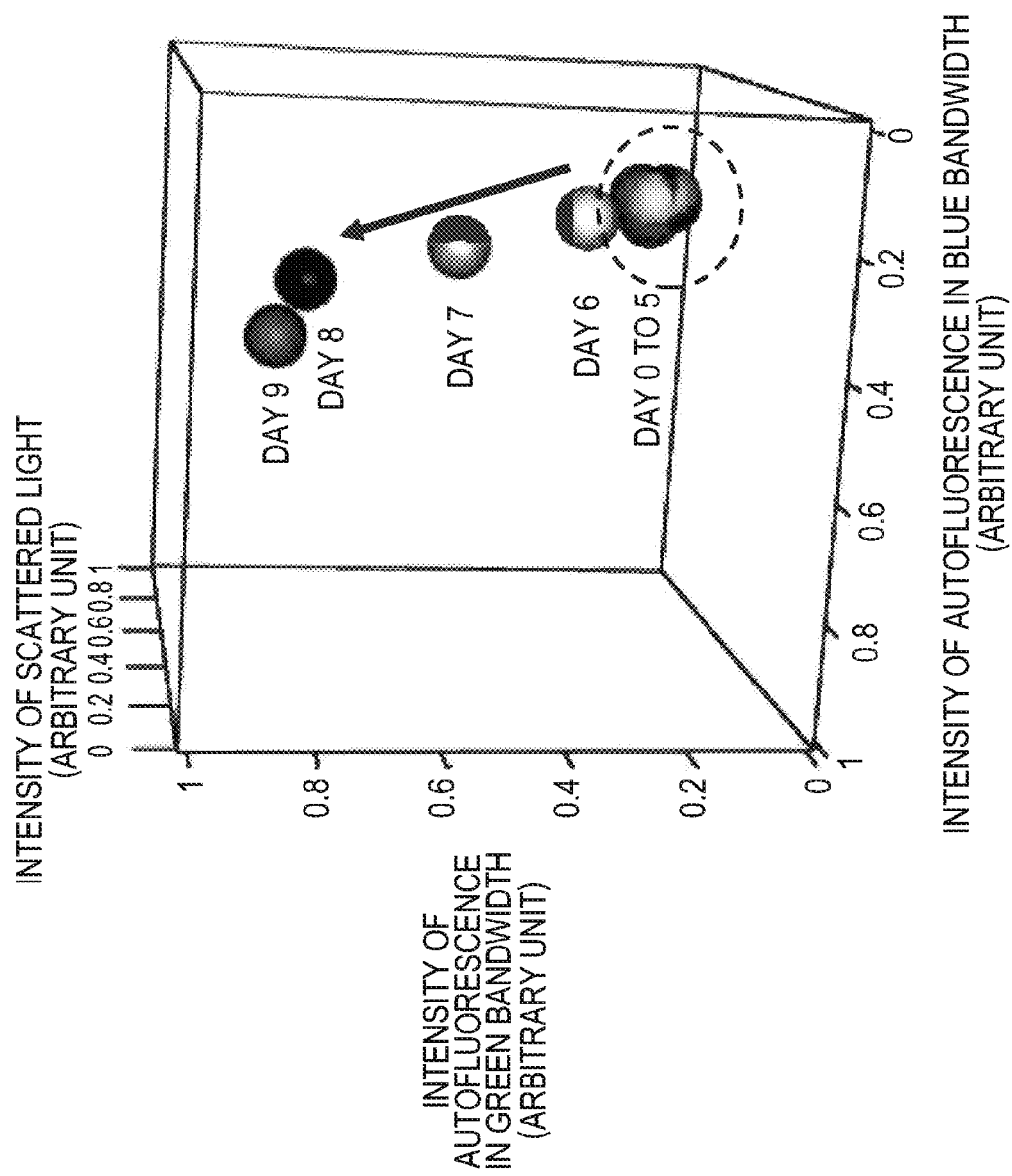
FIG. 10 is a graph showing a relationship among the number of days of cell culture and the intensities of autofluorescence and scattered light according to Example 1.

FIG. 10 shows a three-dimensional graph of the intensities of scattered light and autofluorescence in blue and green bandwidths measured with the particle detector. From Day 0 to Day 5 of the culture, the variations of the coordinates with the measured values of the intensities of scattered light and autofluorescence in blue and green bandwidths as the coordinate components were within a predetermined range. However, from Day 6 of the culture starting decrease of the survival rate, in the coordinates of the measured values, the intensities of autofluorescence in blue and green bandwidths shifted to the higher side, and the intensity of scattered light shifted to the lower side. This probably reflects that the wavelength of autofluorescence at a peak of intensity shifted toward the detection wavelength bandwidth of the fluorescent detector of the particle detector and that the detected small particles increased with a decrease in the survival rate of cells.

Example 2

Reduced nicotinamide adenine dinucleotide (NADH) present in cells and microorganisms emits autofluorescence by irradiation with excitation light. There is a report that protein-binding NADH and free NADH show different fluorescent spectra (for example, see Z. Long, et al., "The real-time quantification of autofluorescence spectrum shape for the monitoring of mitochondrial metabolism", J. Biophotonics, 8, No. 3, 247-257, 2015).

Here, *Escherichia coli* (*E. coli*, ATCC13706) was prepared and cultured in 100 mL of TSB medium in a 300-mL conical flask at 32° C. overnight under aerobic conditions. Subsequently, *E. coli* was harvested with PBS buffer and was washed. The *E. coli* was suspended in PBS buffer again and was sonicated to prepare a homogenate solution. The homogenate solution was centrifuged at 5000 rpm for 10 minutes to remove debris. The supernatant of the centrifuged homogenate solution was centrifuged at 1300 rpm for 30 minutes, and the supernatant was further centrifuged at 1300 rpm for 30 minutes. The resulting supernatant was used as extract of *E. coli*.

The resulting extract was filtered through a gel filtration column (PD-10, GE Healthcare) equilibrated with PBS buffer to give a high molecular weight fraction of NADH having a molecular weight of 5000 or more and a low molecular weight fraction of NADH having a molecular weight of 1000 or less. It is assumed that the high molecular weight fraction of NADH is protein-binding NADH and the low molecular weight fraction of NADH is free NADH.

Figure 11:
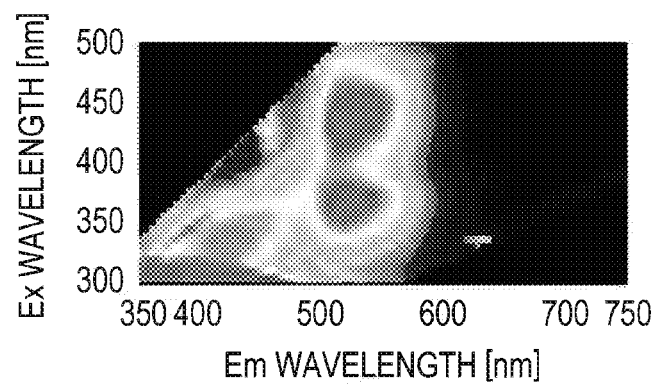
FIG. 11 is an excitation-emission matrix of a high molecular fraction of NADH derived from *Escherichia coli* according to Example 2.
Figure 12:
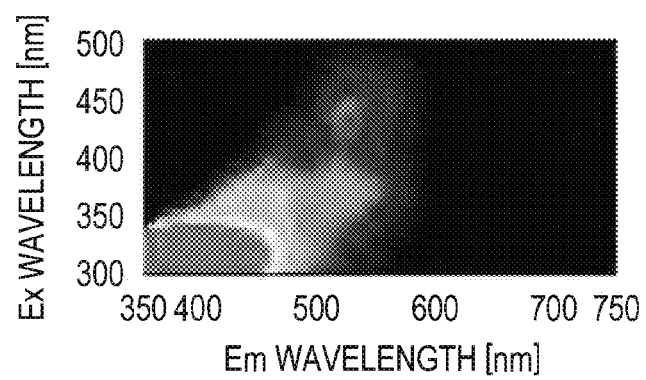
FIG. 12 is an excitation-emission matrix of a low molecular fraction of NADH derived from *Escherichia coli* according to Example 2.

The protein-binding NADH derived from *E. coli* shown in FIG. 11 was analyzed with a spectrofluorometer (FP-8500, manufactured by JASCO Corporation). Analysis of the resulting EEM demonstrated that the peak wavelength of autofluorescence was 430 nm and the peak wavelength of excitation light was 340 nm. In contrast to this, analysis of the EEM of free NADH derived from *E. coli* shown in FIG. 12 demonstrated that the peak wavelength of autofluorescence was 450 nm and the peak wavelength of excitation light was 355 nm. Accordingly, it was suggested that in NADH derived from *E. coli*, the peak wavelength of autofluorescence and the peak wavelength of excitation light shift to the long wavelength side with an increase in free NADH.

*Staphylococcus epidermidis* (ATCC12228) was prepared and cultured in 100 mL of TSB medium in a 300-mL conical flask at 32° C. overnight under aerobic conditions. Subsequently, *Staphylococcus epidermidis* was harvested with PBS buffer and was washed. *Staphylococcus epidermidis* was suspended in PBS buffer again and was disrupted with a disruption kit (OmniLyse Lysis Kit, registered trademark, Claremont BioSolutions, LLC) to give a high molecular weight fraction of NADH having a molecular weight of 5000 or more and a low molecular weight fraction of NADH having a molecular weight of 1000 or less. As described above, it is assumed that the high molecular weight fraction of NADH is protein-binding NADH and the low molecular weight fraction of NADH is free NADH.

Figure 13:
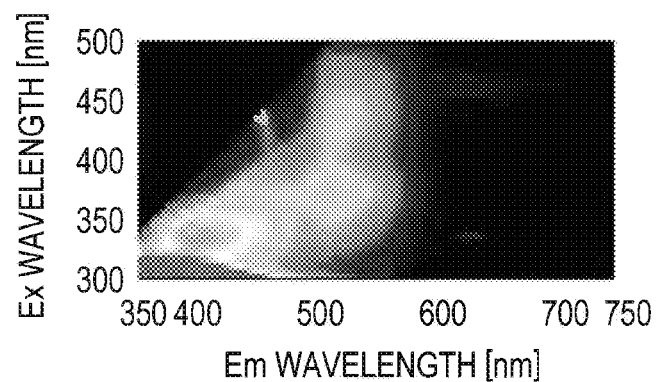
FIG. 13 is an excitation-emission matrix of a high molecular fraction of NADH derived from *Staphylococcus epidermidis* according to Example 2.
Figure 14:
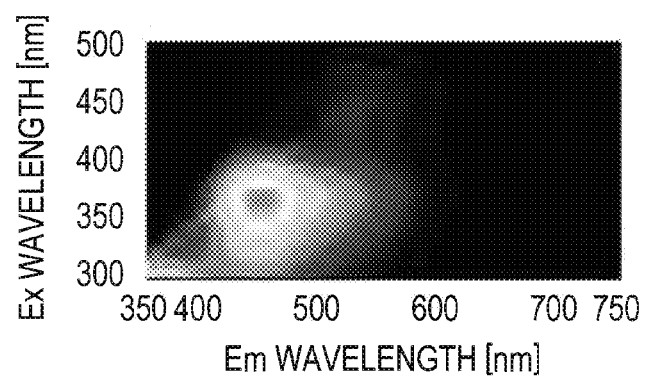
FIG. 14 is an excitation-emission matrix of a low molecular fraction of NADH derived from *Staphylococcus epidermidis* according to Example 2.

The protein-binding NADH derived from *Staphylococcus epidermidis* shown in FIG. 13 was analyzed with a spectrofluorometer (FP-8500, manufactured by JASCO Corporation). Analysis of the resulting EEM demonstrated that the peak wavelength of autofluorescence was 435 nm and the peak wavelength of excitation light was 335 nm. In contrast to this, analysis of the EEM of free NADH derived from *Staphylococcus epidermidis* shown in FIG. 14 demonstrated that the peak wavelength of autofluorescence was 445 nm and the peak wavelength of excitation light was 365 nm. Accordingly, it was suggested that also in NADH derived from *Staphylococcus epidermidis*, the peak wavelength of autofluorescence and the peak wavelength of excitation light shift to the long wavelength side with an increase in free NADH.

As shown in FIG. 8 of Example 1, the peak wavelength of autofluorescence and the peak wavelength of excitation light shifted to the long wavelength side as the proportion of dead cells increases with the number of days of cell culture (in FIG. 8, the cells are not disrupted). It is assumed from the results shown in FIGS. 11 to 14 that this was probably caused by that the reaction of an oxidoreductase binding to NADH is retarded by oxygen deficiency to increase free NADH. Accordingly, it was demonstrated that the shift of the peak wavelength of autofluorescence and the peak wavelength of excitation light to the long wavelength side reflects cell death accompanied by retardation of NADH-dependent oxidoreductase reaction.

Conventionally, in a bioprocess, an oxygen transfer volumetric coefficient may be calculated. A larger value of the oxygen transfer volumetric coefficient indicates a higher oxygen supply capacity of the culture tank. In the case of scale-up of a culture tank, the scale-up conditions are studied so that the oxygen transfer volumetric coefficient is not changed. In contrast to this, since cell death due to oxygen deficiency can be detected using the cell survival rate determining device according to the embodiment, scale-up can be determined without calculating the value of the oxygen transfer volumetric coefficient.

What is claimed is:

1. A cell survival rate determining device, comprising: processing circuitry configured to
   calculate a survival rate of cells in a cell population based on a peak wavelength giving a peak intensity of autofluorescence emitted by the cell population and a peak wavelength of excitation light giving the peak intensity of autofluorescence; and
   determine whether the calculated survival rate of the cells is reliable or not based on an amount of a shift and a direction of the shift per unit time in the peak wavelength of autofluorescence and an amount of a shift and a direction of the shift per unit time in the peak wavelength of excitation light.

2. The cell survival rate determining device according to claim 1, wherein the processing circuitry is further configured to calculate a vector of a sum of a first vector representing the amount of the shift and the direction of the shift per unit time in the peak wavelength of autofluorescence and a second vector representing the amount of the shift and the direction of the shift per unit time in the peak wavelength of excitation light in a coordinate system using the wavelength of autofluorescence and the wavelength of excitation light as coordinate components.

3. The cell survival rate determining device according to claim 2, wherein the processing circuitry is further configured to determine that the calculated survival rate of cells is reliable when a size of the vector of the sum is not lower than a predetermined threshold and a direction of the vector of the sum is within a predetermined range.

4. The cell survival rate determining device according to claim 2, wherein the processing circuitry is further configured to determine that the calculated survival rate of cells is unreliable when a size of the vector of the sum is not lower than a predetermined threshold and a direction of the vector of the sum is out of a predetermined range.

5. The cell survival rate determining device according to claim 1, wherein the processing circuitry is further configured to calculate the survival rate of the cells in the cell population, which includes Chinese hamster ovary (CHO) cells, based on the peak wavelength giving the peak intensity of autofluorescence emitted by the cell population of the CHO cells and the peak wavelength of excitation light giving the peak intensity of autofluorescence.

6. A cell survival rate determining method, comprising:
   calculating, by processing circuitry, a survival rate of cells in a cell population based on a peak wavelength giving a peak intensity of autofluorescence emitted by the cell population and a peak wavelength of excitation light giving the peak intensity of autofluorescence; and
   determining, by the processing circuitry, whether the calculated survival rate of the cells is reliable or not based on an amount of a shift and a direction of the shift per unit time in the peak wavelength of autofluorescence and an amount of a shift and a direction of the shift per unit time in the peak wavelength of excitation light.

7. The method of claim 6, further comprising calculating a vector of a sum of a first vector representing the amount of the shift and the direction of the shift per unit time in the peak wavelength of autofluorescence and a second vector representing the amount of the shift and the direction of the shift per unit time in the peak wavelength of excitation light in a coordinate system using the wavelength of autofluorescence and the wavelength of excitation light as coordinate components.

8. The method of claim 7, wherein the determining step comprises determining that the calculated survival rate of cells is reliable when a size of the vector of the sum is not lower than a predetermined threshold and a direction of the vector of the sum is within a predetermined range.

9. The method of claim 7, wherein the determining step comprises determining that the calculated survival rate of cells is unreliable when a size of the vector of the sum is not lower than a predetermined threshold and a direction of the vector of the sum is out of a predetermined range.

10. The method of claim 6, wherein the calculating step comprises calculating the survival rate of the cells in the cell population, which includes Chinese hamster ovary (CHO) cells, based on the peak wavelength giving the peak intensity of autofluorescence emitted by the cell population of the CHO cells and the peak wavelength of excitation light giving the peak intensity of autofluorescence.

* * * * *